United States Patent [19]
Uecker

[11] 3,937,224
[45] Feb. 10, 1976

[54] COLOSTOMY CATHETER

[76] Inventor: Ronald L. Uecker, 915 Grant St., Wausau, Wis. 54401

[22] Filed: Apr. 11, 1974

[21] Appl. No.: 459,892

[52] U.S. Cl. ............................ 128/348; 128/349 B
[51] Int. Cl.² ........................................ A61M 25/00
[58] Field of Search ........ 128/348, 349 R B, 350 R, 128/214 B, 214.2, 344, DIG. 9, 349

[56] References Cited
UNITED STATES PATENTS

| | | |
|---|---|---|
| 1,060,665 | 5/1913 | Bell .................................. 128/349 R |
| 3,169,528 | 2/1965 | Knox et al. ...................... 128/350 R |
| 3,435,824 | 10/1966 | Gamponia ...................... 128/349 B |
| 3,618,613 | 11/1971 | Schulte ............................. 128/348 |
| 3,628,813 | 12/1971 | Lee .................................... 128/348 |
| 3,811,450 | 5/1974 | Lord ................................. 129/349 B |

Primary Examiner—Robert W. Michell
Assistant Examiner—Henry S. Layton
Attorney, Agent, or Firm—Jacques M. Dulin

[57] ABSTRACT

Colostomy-type catheter devices having multiple sealing balloons dispersed adjacent each end of a single tube, and having a side arm communicating with the lumen of the tube through which fluids may be introduced or withdrawn. Each balloon may have its own inflation lumen or a common lumen. The catheter may be preformed in the shape of a loop, U, Ω, or other form, or contain means embedded in the catheter wall, such as soft wire, that permits the catheter upon a use to be so formed. An external form may also be used to hold the catheter in such shape during use. Clamps may be used to permit sequential or simultaneous infusion of each branch of the catheter, or operate as a bypass from one branch to the other without drainage.

12 Claims, 7 Drawing Figures

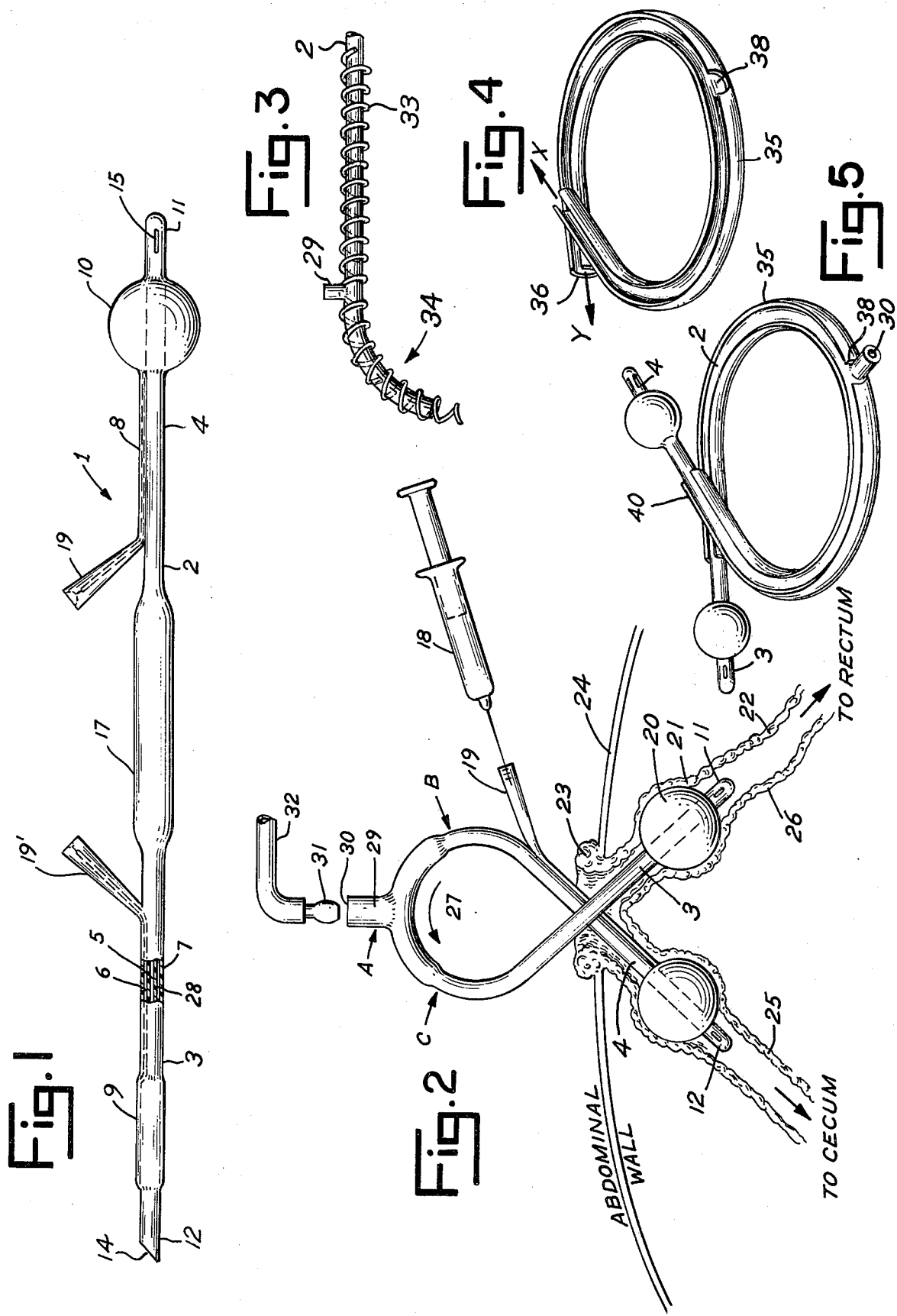

COLOSTOMY CATHETER

FIELD

This invention relates to catheters, particularly those having multiple inflatable sealing balloons for internal use for sealing a central tube in a body passage or opening. More particularly, the catheters of this invention relate to preformed or formable catheters for use in colostomy procedures, or procedures in which drainage or infusion of one limb of a body passage may be selectively required while a second limb remains selectively sealed, or, at the option of the doctor, may be permitted to communicate with the first limb.

BACKGROUND

There are many surgical procedures requiring intercepting a subcutaneous vessel or passage in a manner that forms an opening to the surface and isolation of two limbs. These limbs may be treated separately or sequentially, e.g., by drainage, infusion, injection, x-ray examination and the like, yet often require intermittent communication therebetween to provide for normal bodily functions. Examples are colostomy-type procedures, extracorporeal blood shunts, such as A-V shunts, hemodialysis, and the like.

More particularly, some diseases of the distal colon, e.g., diverticulitis and carcinoma, often require a temporary diverting colostomy to put the distal colon at rest for a period of time. In the colostomy procedure, the ends of the bisected colon, or a slit loop of the colon, are brought out to the skin surface of the ventral abdomen, diverting the fecal stream outside the body.

X-ray examination of the colon, by instillation of a water suspension of barium sulfate, or other liquid contrast agent, is frequently necessary while the colostomy is functioning. Currently, it is usual to introduce the barium sulfate suspension via separate catheters placed in the colostomy openings and in the rectum. Such individual catheters require sequential use, with the lower colon usually filled via the rectal catheter and using a balloon or catheter plug to seal the colostomy opening to prevent spill onto the skin. Following this, the proximal colon is examined via a second balloon catheter introduced into the other colostomy opening, the enema bag tubing having been switched from the rectal catheter to the colostomy catheter. The entire procedure requires several clamps: (1) to close the colostomy catheter used as a plug, (2) to close the rectal catheter when the enema bag tubing is switched to the colostomy catheter, and (3) to keep the colostomy catheter closed prior to use. The considerable time necessary to this sequence increases discomfort to the patient.

There is, therefore, a need for a catheter device, suitable, inter alia, for colostomy procedures and the like, which is simple of construction yet avoids the disadvantages of the prior, multiple catheter or tube procedures.

THE INVENTION

OBJECTS

It is among the objects of this invention to provide an improved catheter construction.

It is another object to provide an improved catheter having plural inflatable sealing balloons for placement in different areas of a single body passage or plural passages, openings or cavities.

It is another object to provide an improved colostomy catheter that selectively permits communication between limbs or drainage from one or both.

It is another object to provide an improved catheter having sealing balloons disposed adjacent opposite ends thereof, and having a communication means to the interior of the central cannula.

It is another object to provide a formable or preformed catheter that is or can be shaped for such procedures, such as into the form of a loop, U, or Ω configuration.

It is another object to provide a retaining means that can permit holding the catheter in a desired configuration during use, such as in a loop, U, Ω, or other convenient shape.

Still other objects will be evident in the description which follows.

SUMMARY

The catheter of this invention, in a principal embodiment, may be characterized as a double-ended catheter, having individual or interconnected sealing balloons adjacent the ends thereof, and having a central cannula or lumen from end to end. In another embodiment, a side arm tube communicates with the central lumen, forming therewith a generally T-shaped configuration. The side arm may be originally sealed or unsealed, and provides means for drainage or infusion of one or more of the two limbs of the catheter. The side arm may be the same diameter as the central lumen, or may be smaller or larger, or otherwise adapted to permit interconnection with a variety of devices, such as enema bags, drainage bags, suction devices, irrigation devices for solutions, and the like.

The catheter of this invention may be made of any physiologically compatible material, such as rubber or plastic. Particularly preferred are plastics of the vinyl or silicone types, such as polyvinyl-chloride, polyethylene, polystyrene, polypropylene, or any of the silicone polymers conventionally used for such devices. It is important that the catheter be appropriately sized for the body passage, opening, or organ, and that the balloon not cause or promote tissue necrosis. Balloon construction of the type shown in U.S. Pat. No. 3,734,100, among others, is suitable for the catheters of this invention. The catheter material may be made x-ray opaque to facilitate visualization at fluoroscopy or on x-ray films.

In another embodiment, the catheter may be preformed, or have means for forming it into a special configuration, such as a loop, U-shape, Ω-shape, or other appropriate shape to reduce patient discomfort. This orients the catheter tips and balloons to minimize tip blockage and tissue damage.

The catheter may be preformed by curing or heat-setting the rubber or plastic from which the body is formed. The entire catheter may be preformed, or only the medial portion formed with the distal portions left relatively flexible, as by differential curing along the catheter length. The tips are generally firm to prevent collapse or closure in use, but are not sharp, to prevent tissue damage.

The catheter may contain forming means, such as soft wire embedded in the walls. Alternately the catheter may be retained in use in a special holder of plastic, rubber, metal or the like.

FIGURES

The description has reference to the drawings in which:

FIG. 1 illustrates a plan view, partly in section, of one embodiment of the colostomy catheter of this invention;

FIG. 2 illustrates another embodiment, having central cannula or lumen communication means, in operation;

FIG. 3 is a view of an embodiment of a holder for the catheters of this invention, here a soft wire coil that can be formed to the shape desired;

FIG. 4 is a perspective view of another embodiment of a holder for the catheters of this invention;

FIG. 5 shows in plan view a holder of the type in FIG. 4 in use with the catheter snap-fit therein;

DETAILED DESCRIPTION

Figure 6:
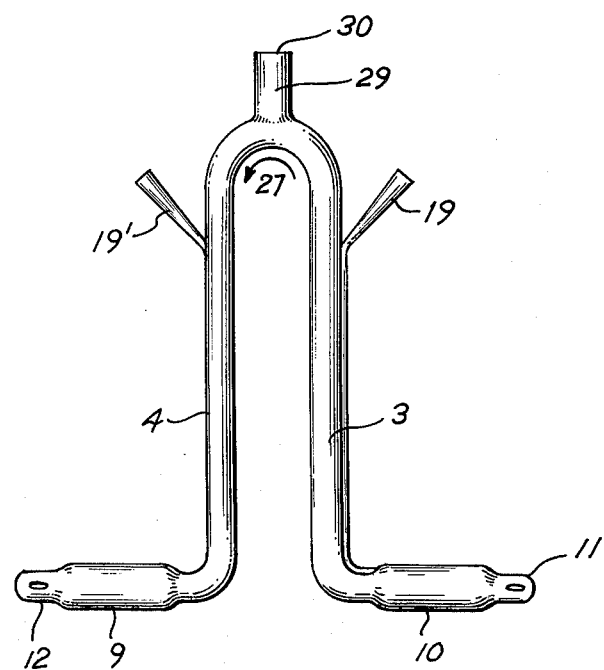
FIG. 6 shows in plan view and inverted U-shaped catheter.

Referring to FIG. 1, the catheter 1 comprises a generally elongated tube 2 having a plurality of limbs, here a first limb 3 and a second limb 4. As shown in the broken-away portion of FIG. 1, the tube has a central lumen 5 and inflation lumen 6. The inflation lumen 6 may be disposed within the catheter wall 7 or may comprise a tube 8 integrally secured to or separate from the catheter tube 2. The inflation lumen 6 and tube 8 communicate with expansible sealing balloons 9 (shown uninflated) and 10 (shown in the inflated condition). These balloons are formed as an integral part of the catheter, or may be separately formed and secured to the exterior of the catheter tube.

The tips of the tube 11 and 12 may be the same or different (as shown), and are selected to be adapted to the particular surgical or treatment procedure employed. For example, a slantcut tip 12 has an axial end opening 13 which may be used to permit rapid drainage, infusion, or communication between limbs 3 and 4. The tip edges 14 are smoothed to permit ease of insertion without tissue damage. Rounded tip 11 may be apertured at the sides 15 and/or the tip 16. The rounded tip provides a reduced diameter portion for ease of entry, and substantially little or no tissue damage in use.

The central portion 17 may have the same interior and exterior diameter as the limbs 3 and 4, or as shown in FIG. 1 may be enlarged throughout that portion which is generally exposed exterior of the body.

As best seen in FIG. 2, inflation of a balloon is accomplished in a conventional manner. Syringe 18 is inserted in the free end 19 of the inflation tube and compressed to fill the balloon with a prescribed amount air, saline solution, or water to provide a seal between the balloon surface 20 and the tissue walls 21. Typically, for colostomy use, the balloons may have a capacity ranging from 60–120 cc, and the catheter body O.D. may be from 5–15 mm with the overall length being 15 – 25 inches. The free end of the inflation lumen may be adapted for connection to inflation devices, as with a rubber or plastic plug which is pierced by a syringe needle, or by a special valve of conventional type.

In operation, referring now to FIG. 2, which is a transverse cross section of the anterior abdomen, the invention works as follows: After surgically isolating the colon lumen 22 and providing colostomy opening 23 through the skin 24, the limbs 3, 4 of the catheter are inserted into the branches 25, 26 of the colon and the balloons 9, 10 are inflated. The catheter tips and limbs may be inserted sequentially or simultaneously. Likewise, the balloons may be inflated sequentially by inflation syringe 18, or the inflation lumen may communicate with both balloons so that they may be inflated simultaneously through the inflation tube 19, as shown in FIG. 2.

As shown in FIG. 2, we prefer the medial portion of the catheter to form a loop 27 so that tips 11, 12 are oriented generally parallel to the axis of the colon lumen in place in their respective branches 25, 26. This assists in reducing patient discomfort and preventing the tips from damaging the lumen by scraping or perforating it. This orientation also assists in reducing the possibility of plugging the tip openings permitting better drainage, infusion, and the like.

Thus, an important embodiment of this invention is a catheter having a medial loop, as illustrated in FIG. 2. This is the preferred embodiment, as compared to that of FIG. 1. However, when there is little chance for colon damage or tip opening blockage, the preformed loop configuration need not be employed. In such instances the catheter of FIG. 1 can be formed, or retained in a U or $\Omega$ (omega) shape at the time of use.

Figure 7:
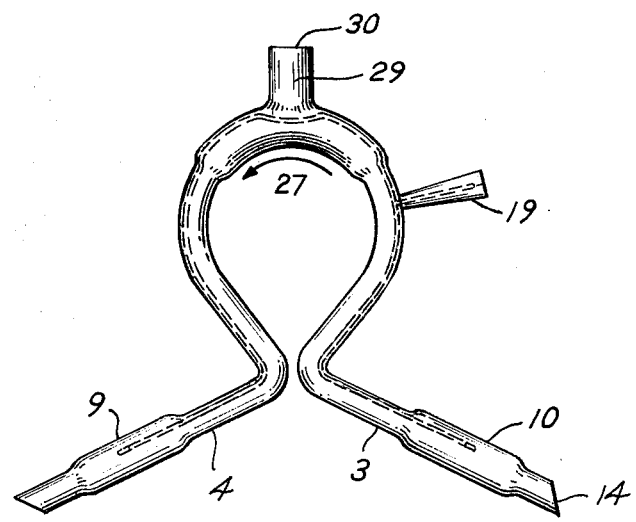
FIG. 7 shows in plan view an $\Omega$-shaped catheter.

This invention also includes catheters preformed during the manufacture in the loop, U or $\Omega$ shapes, as shown in FIGS. 2, 6 and 7. This may be done by forming a partially cured silicone rubber tube in the loop, U or $\Omega$ shape, and completing the cure while the tube is retained in that shape. Similarly, thermoplastic or thermosetting plastic tubes can be formed or reformed into the desired shape. An alternate method of manufacture is to cast the tubes in the loop or other shape over a flexible mandrel, and subsequent to cure or cooling, withdrawing the mandrel.

In another embodiment, the straight tube of FIG. 1 is formed with one or more soft or bendable wires 28 (FIG. 1) embedded in the catheter wall 7. The catheter can then be bent into the desired form during the operating or treatment procedures, and the soft wire will hold the catheter in the formed configuration. After use, the catheter can be withdrawn and straightened, or reformed for another use. The soft, bendable wire(s) may be oriented parallel to the cannula axis, or may be in the form of a spiral, in the nature of a bendable type of cylindrical springshaped construction embedded in the catheter wall.

As seen in FIG. 3, another manner of formation of the catheter of FIG. 1 into a loop during use (as distinct from a preformed catheter as in FIG. 2) employs a bendable soft wire spring 33. The bendable spring is slipped over the medial portion 17 and bent to form the catheter into the configuration desired as shown at 34 in FIG. 3. Although bendable, the wire 33 is sufficiently strong to retain the curve 34 imparted thereto against the natural return force of the catheter. Alternatively, a disposable or reusable plastic or metal loop-shaped retainer 35 may be used. Such retainer is conveniently C-shaped in cross section as at 36 so that the resilient catheter 2 snaps into the retainer via slot 37, and is retained in a loop, U or $\Omega$ configuration during use. Notch 38 is provided to receive the side arm 29. Preferably the ends 39, 40 of the retainer overlap, rather than lie in a common plane, so that the ends 3, 4 of the catheter do not interfere with each other. The retainer of FIGS. 4 and 5 forms a generally non-planar helical loop as shown by arrows X, Y in FIG. 5, but may be planar, such as U-shaped, Ω-shaped, or the like.

Continuing with the operational description, the inflated balloons provide retention of the catheters in position and sealing of the colostomy opening. For example, during examination of the colon, barium sulfate contrast solution is introduced via the rectum and passes upward through colon limb 26. The catheter of this invention provides a closed bypass of the colostomy opening to limb 25, preventing spill onto the skin, and permitting examination of both sides (limbs 25, 26 in FIG. 2) of the colon. Following the x-ray examination, the barium sulfate solution or other liquid contrast agent can be withdrawn by gravity suction back into the enema bag, or the patent can be allowed to evacuate per rectum. The catheter is then left in place as a plug, or removed after deflating its balloons.

If the barium sulfate contrast solution or other liquid contrast agent cannot be introduced via the rectum because of obstruction in the distal colon, either or both sides of the colon can be filled directly through the colostomy catheter 1, using the central side arm 29. The side arm is molded into the medial portion 17 of the catheter. The end 30 of the side arm may be provided closed so the catheter is useful as a bypass device as described above. In the alternative, the side arm may be open at end 30, and a clamp used at position A to provide the bypass arrangement.

For the distal colon obstruction situation, the side arm is adapted to accept a tip 31 which connects via tube 32 to the contrast solution source. After introducing the solution, the tube 32 can be connected to an enema bag. Following the x-ray examination, gravity suction can be used to empty the bowel back into the enema bag, following which the side arm opening may be plugged. Alternatively, the balloons are deflated and the catheter removed.

Where examination of only the distal portion of the colon is desired, the catheter may be clamped at position B. Conversely, where only the ascending colon, small bowel, appendix or the like is to be examined, the catheter is clamped closed at C, and the solution introduced and evacuated through the side arm 29.

Likewise, simultaneous or sequential irrigation or drainage of the body passage, organ or opening may be accomplished by use of the clamps A, B, and C.

It should be understood that various modifications within the scope of this invention can be made by one of ordinary skill in the art without departing from the spirit thereof. I therefore wish my invention to be defined by the scope of the appended claims as broadly as the prior art will permit, and in view of this specification if need be.

I claim:

1. An improved diagnostic catheter assembly for use in colostomies comprising:
    a. an elongated, generally cylindrical body portion having generally annular walls and a central passage extending from end to end of said body and communicating with openings in said ends;
    b. a plurality of sealing balloon members, at least one of which is disposed on said body adjacent each end thereof, and defining a medial portion therebetween;
    c. an inflation lumen disposed in association with said body wall communicating with a sealing balloon member, and having means for permitting inflation of said balloon therethrough disposed medially of said balloon;
    d. said medial portion includes a side arm member having a passage communicating with said central passage;
    e. said sealing balloon members being adapted to provide sealing of a colostomy opening when inflated into contact with walls of the intestine;
    f. said side arm member is adapted for connection to fluid conduit means external of a patient's body, and
    g. means for selectively forming the medial portion of said catheter into a curved shape and to retain said shape after forming.

2. A catheter as in claim 1 wherein said selective forming means includes a bendable material having the property of being manually formable into a selected shape upon application of force thereto and retaining said shape after said forming, and said material is disposed in the wall of said body.

3. A catheter as in claim 1 wherein said selective forming means includes removable means for retaining said catheter in a predetermined shape.

4. A catheter as in claim 3 wherein said retaining means is a form having body securing portions generally C-shaped in cross section.

5. A catheter as in claim 1 wherein said selective forming means includes a bendable coil having the property of being manually formable into a selected shape upon application of force thereto and retaining said shape after said forming, and said coil is adapted to fit over the medial portion of said catheter.

6. A catheter as in claim 1 which is formed prior to use into a generally curved shape selected from shapes characterizable as a medial loop, U-like, and Ω-like.

7. A catheter as in claim 1 wherein at least one of said body end openings communicates with a tip portion adapted for ease of insertion.

8. A catheter as in claim 7 wherein said tip is generally rounded and has a plurality of openings therein.

9. A catheter as in claim 7 wherein said tip is generally cut transverse to the axis of said central passage.

10. A catheter as in claim 1 wherein said selective forming means is a ductile material.

11. A catheter as in claim 10 wherein said ductile material is soft iron wire.

12. A catheter as in claim 1 wherein said selective forming means includes body materials selected from natural and synthetic curable rubber, and thermoplastic and thermosetting plastic compositions.

* * * * *